(12) United States Patent
Rangel et al.

(10) Patent No.: US 9,744,403 B2
(45) Date of Patent: Aug. 29, 2017

(54) ACTIVITY TRACKING RACQUET ATTACHMENT DEVICE

(71) Applicants: Jorge H. Rangel, Miami, FL (US); Gerardo Marvez, Miami, FL (US)

(72) Inventors: Jorge H. Rangel, Miami, FL (US); Gerardo Marvez, Miami, FL (US)

( * ) Notice: Subject to any disclaimer, the term of this patent is extended or adjusted under 35 U.S.C. 154(b) by 582 days.

(21) Appl. No.: 14/303,680

(22) Filed: Jun. 13, 2014

(65) Prior Publication Data
US 2015/0360082 A1 Dec. 17, 2015

(51) Int. Cl.
| | | |
|---|---|---|
| *G04B 47/00* | (2006.01) |
| *A63B 49/08* | (2015.01) |
| *A63B 24/00* | (2006.01) |
| *A63B 71/06* | (2006.01) |
| *A63B 69/38* | (2006.01) |
| *A61B 5/103* | (2006.01) |
| *G09F 23/00* | (2006.01) |
| *A61B 5/00* | (2006.01) |
| *A63B 60/16* | (2015.01) |
| *G06K 9/00* | (2006.01) |

(52) U.S. Cl.
CPC .......... *A63B 24/0062* (2013.01); *A61B 5/103* (2013.01); *A61B 5/4866* (2013.01); *A61B 5/6895* (2013.01); *A63B 49/08* (2013.01); *A63B 60/16* (2015.10); *A63B 69/38* (2013.01); *A63B 71/0619* (2013.01); *A63B 71/0622* (2013.01); *A63B 71/0686* (2013.01); *G09F 23/0066* (2013.01); *A63B 2071/065* (2013.01); *A63B 2071/0625* (2013.01); *A63B 2071/0627* (2013.01); *A63B 2071/0647* (2013.01); *A63B 2071/0658* (2013.01); *A63B 2071/0694* (2013.01); *A63B 2220/40* (2013.01); *A63B 2220/62* (2013.01); *A63B 2220/803* (2013.01); *A63B 2220/833* (2013.01); *A63B 2225/20* (2013.01); *A63B 2225/50* (2013.01); *A63B 2230/75* (2013.01); *G06K 9/00335* (2013.01)

(58) Field of Classification Search
None
See application file for complete search history.

(56) References Cited

U.S. PATENT DOCUMENTS

| | | | | |
|---|---|---|---|---|
| 5,439,217 A | * | 8/1995 | Ganger, Sr. | A63B 69/3635 473/199 |
| 5,642,882 A | * | 7/1997 | Guerzini | A63B 60/16 473/300 |
| 5,646,911 A | * | 7/1997 | Davis | A63B 71/0622 368/10 |

(Continued)

*Primary Examiner* — Lawrence Galka

(57) ABSTRACT

An activity tracking racquet attachment device tracks activity such as calories burned over a period of using a racquet to which the device is attached. The device includes a housing having a first face and a perimeter sidewall extending from and around the first face. A processor is coupled to the housing. A motion detector is coupled to the housing such that the motion detector detects movement of the housing. The motion detector is communicatively coupled to the processor wherein the processor receives motion data from the motion detector. A coupler is coupled to and extends from a second face of the housing coupling the housing to an end of a handle of a racquet such that the first face of the housing faces outwardly from the end of the handle.

13 Claims, 4 Drawing Sheets

(56) References Cited

U.S. PATENT DOCUMENTS

| | | | |
|---|---|---|---|
| 5,757,266 A * | 5/1998 | Rider | A63B 69/38 |
| | | | 273/317.4 |
| 6,270,434 B1 | 8/2001 | Shaw | |
| D458,171 S | 6/2002 | Lin | |
| 6,409,616 B1 * | 6/2002 | Lin | A63B 69/38 |
| | | | 473/463 |
| 6,565,449 B2 * | 5/2003 | Buhler | A63B 24/0021 |
| | | | 473/151 |
| 7,326,133 B1 | 2/2008 | Choi | |
| 7,427,245 B2 | 9/2008 | Hickey | |
| 2005/0054457 A1 * | 3/2005 | Eyestone | A63B 15/00 |
| | | | 473/221 |
| 2007/0073482 A1 * | 3/2007 | Churchill | G01S 3/36 |
| | | | 701/492 |
| 2010/0267502 A1 * | 10/2010 | Kaufman | A63B 49/08 |
| | | | 473/549 |
| 2012/0116548 A1 * | 5/2012 | Goree | A61B 5/1118 |
| | | | 700/90 |
| 2013/0073248 A1 * | 3/2013 | Perkins | A61B 5/6895 |
| | | | 702/141 |
| 2013/0095941 A1 * | 4/2013 | Bentley | H05K 5/0204 |
| | | | 473/223 |

\* cited by examiner

ACTIVITY TRACKING RACQUET ATTACHMENT DEVICE

BACKGROUND OF THE DISCLOSURE

Field of the Disclosure

The disclosure relates to racquet attachment devices and more particularly pertains to a new racquet attachment device for tracking activity such as calories burned over a period of using a racquet to which the device is attached.

SUMMARY OF THE DISCLOSURE

An embodiment of the disclosure meets the needs presented above by generally comprising a housing having a first face and a perimeter sidewall extending from and around the first face. A processor is coupled to the housing. A motion detector is coupled to the housing such that the motion detector detects movement of the housing. The motion detector is communicatively coupled to the processor wherein the processor receives motion data from the motion detector. A coupler is coupled to and extends from a second face of the housing coupling the housing to an end of a handle of a racquet such that the first face of the housing faces outwardly from the end of the handle.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
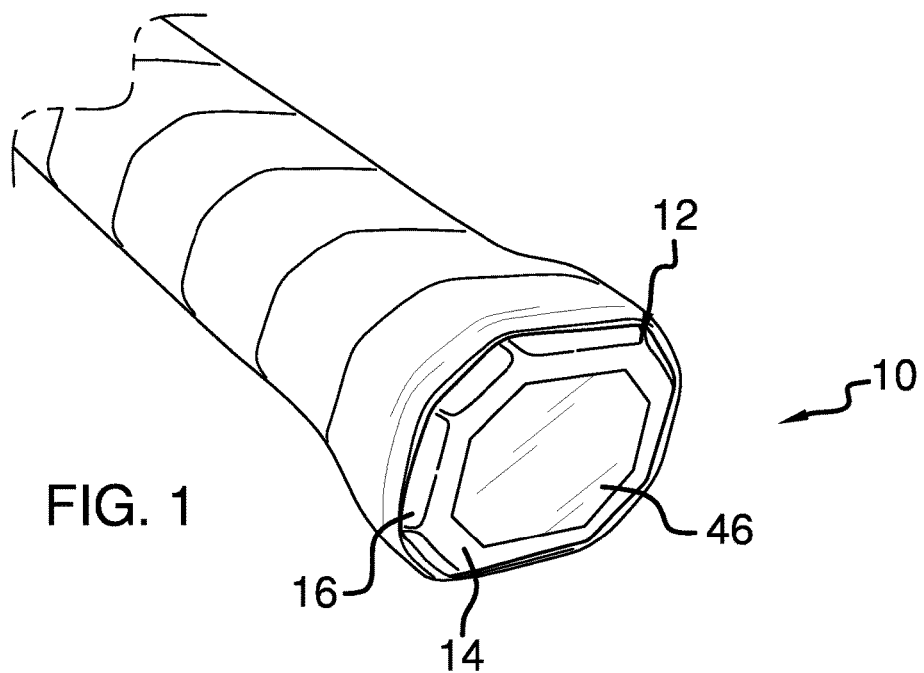
FIG. 1 is a top front side perspective view of a activity tracking racquet attachment device according to an embodiment of the disclosure.

With reference now to the drawings, and in particular to FIGS. 1 through 8 thereof, a new racquet attachment device embodying the principles and concepts of an embodiment of the disclosure and generally designated by the reference numeral 10 will be described.

Figure 6:
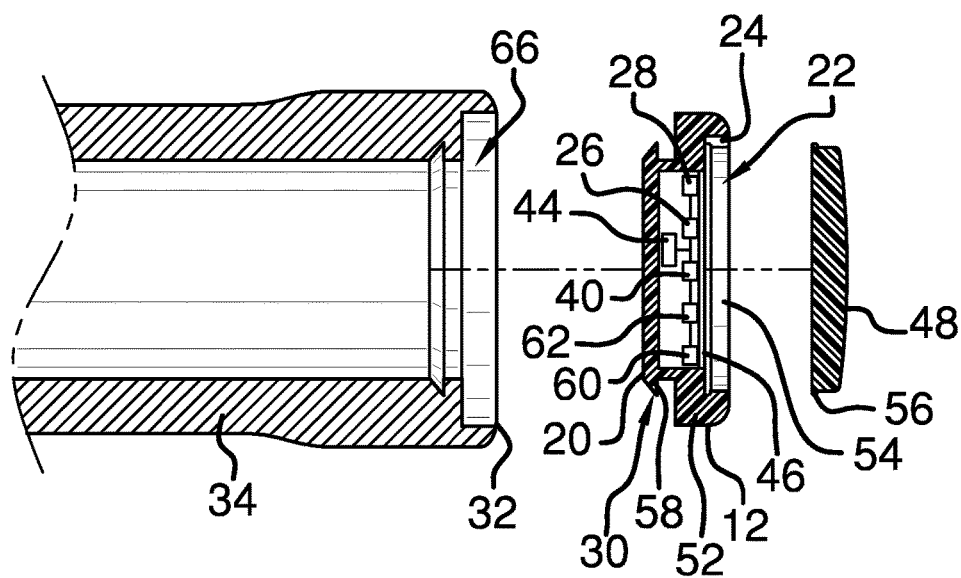
FIG. 6 is a partially exploded cross-sectional view of an embodiment of the disclosure taken along a longitudinal axis of a racquet handle.
Figure 7:
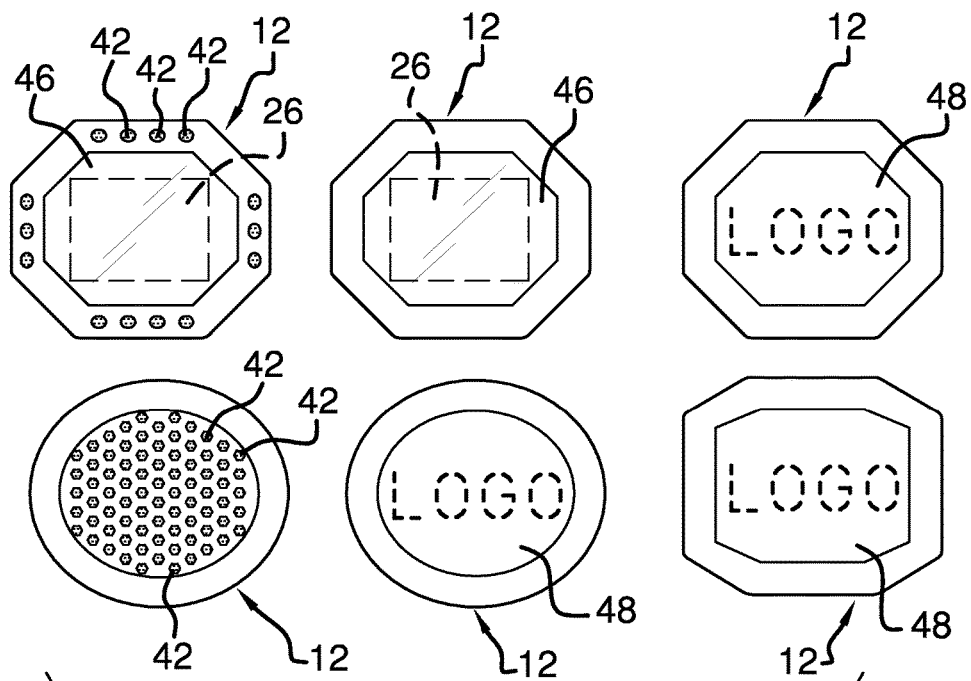
FIG. 7 is a front view of embodiments of the disclosure designed for variously shaped racquet handles.
Figure 8:
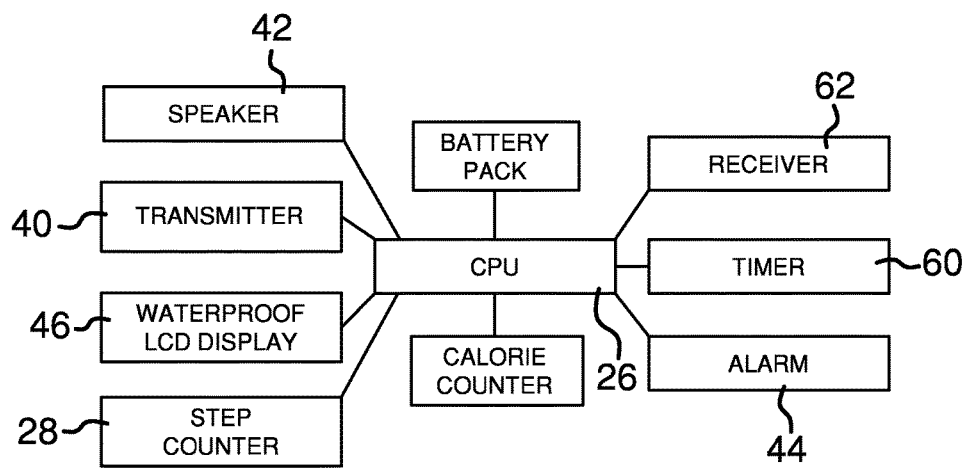
FIG. 8 is a schematic view of an embodiment of the disclosure.

As best illustrated in FIGS. 1 through 8, the activity tracking racquet attachment device 10 generally comprises a housing 12 having a first face 14. A perimeter sidewall 16 extends from and around the first face 14. The perimeter sidewall 16 is angled relative to the first face 14 such that the perimeter sidewall 16 extends outward laterally from a peripheral edge 18 of the first face 14 of the housing 12 and towards a second face 20 of the housing 12. The housing 12 is structured to define a well 22 extending into the first face 14 of the housing 12. The housing 12 has a notch 24 extending from the well 22. A processor 26 is coupled to the housing 12. A motion detector 28 of conventional design used in pedometers, positional monitors, and the like, is coupled to the housing 12 such that the motion detector 28 detects movement of the housing 12. The motion detector 28 is communicatively coupled to the processor 26 wherein the processor 26 receives motion data from the motion detector 28. The processor 26 may process the motion data to determine calories burned corresponding to the motion data. A coupler 30 is coupled to and extends from the second face 20 of the housing 12 wherein the housing 12 is configured for being coupled to an end 32 of a handle 34 of a racquet such that the first face 14 of the housing 12 faces outwardly from the end 32 of the handle 34 of the racquet. The coupler 30 may be a circumferential projection 58 offset from the second face 20 of the housing 12. A cavity 66 extending into the end 32 of the handle 34 may be complementary in shape to the housing 12 to receive the projection 58 and abut the second face 20 of the housing 12 substantially against the end 32 of the handle 34. As shown in FIG. 7, the outer peripheral edge 18 of the first face 14 of the housing 12 may take various forms corresponding to the shape of the end 32 of the handle 34 such that the housing 12 blends in and appears as an integrated piece of the racquet.

A transmitter 40 may be coupled to the housing 12. The transmitter 40 is communicatively coupled to the processor 26 wherein the processor 26 transmits the motion data to an extrinsic apparatus such as a smartphone, computer, electronic tablet, or the like. The transmitter 40 may transmit the motion data using a wireless personal access network, the internet, or the like. A speaker 42 may be coupled to the housing 12 and operationally coupled to the processor 26 wherein the processor 26 broadcasts audio through the speaker 42 The audio broadcast may correspond to an alarm 44 related to a timer set to measure a duration of time, measurement of a number of calories to be burned, or the like. The speaker 42 may also be used in conjunction with the processor and a media storage device coupled to the housing 12 to play songs or the like.

As shown in FIG. 6, a connection port 80, such as a universal serial bus, mini universal serial bus, or the like, may be coupled to the second face 20 of the housing 12. The connection port 80 may be provided with or as an alternative to the transmitter 40 as a way of communication to upload program modifications, updates, firmware, or the like, or to download stored motion data to an extrinsic apparatus through a hard connection either by a wire or direct plug into the extrinsic apparatus.

A display screen 46 is coupled to the housing 12. The display screen 46 is operationally coupled to the processor 26 wherein the processor 26 displays images on the display screen 46. The images may correspond to the motion data, time elapsed, time expired, operational control of the device 10, song selection, or other functions of the device 10. As shown in FIG. 1, the display screen 46 may be flush with the first face 14. Alternatively, the display screen 46 is parallel to and inset from the first face 14 of the housing 12 and positioned in the well 22 wherein the display screen 46 is visible within the well 22 yet substantially protected from being damaged during use of the racquet 36. A cap 48 is positionable in the well 22 such that the cap 48 covers the display screen 46. The cap 48 is removably coupled to the housing 12 for selectively exposing the display screen 46. An exposed portion of a perimeter edge 50 of the cap 48 is accessible through the notch 24 to facilitate removal of the cap 48 from the well 22. A groove 52 extends into an inwardly facing wall 54 defining the well 22. The groove 52 is positioned in spaced relationship to the first face 14 of the housing 12. The groove 52 extends a full length around the inwardly facing wall 54. A lip 56 extends outwardly from the perimeter edge 50 of the cap 48. The lip 56 is positionable in the groove 52 coupling the cap 48 to the housing 12. The lip 56 may extend fully around the perimeter edge 50 of the cap 48. Interchangeable caps 48 may be provided with various logos.

A timer 60 may be coupled to the housing 12 and communicatively coupled to the processor 26 to perform the various functions described above. A receiver 62 may also be coupled to the housing 12 and communicatively coupled to the processor 26 wherein the processor 26 is controllable from transmissions received by the receiver 62. Thus, the device 10 may be controlled using the extrinsic apparatus.

Figure 2:
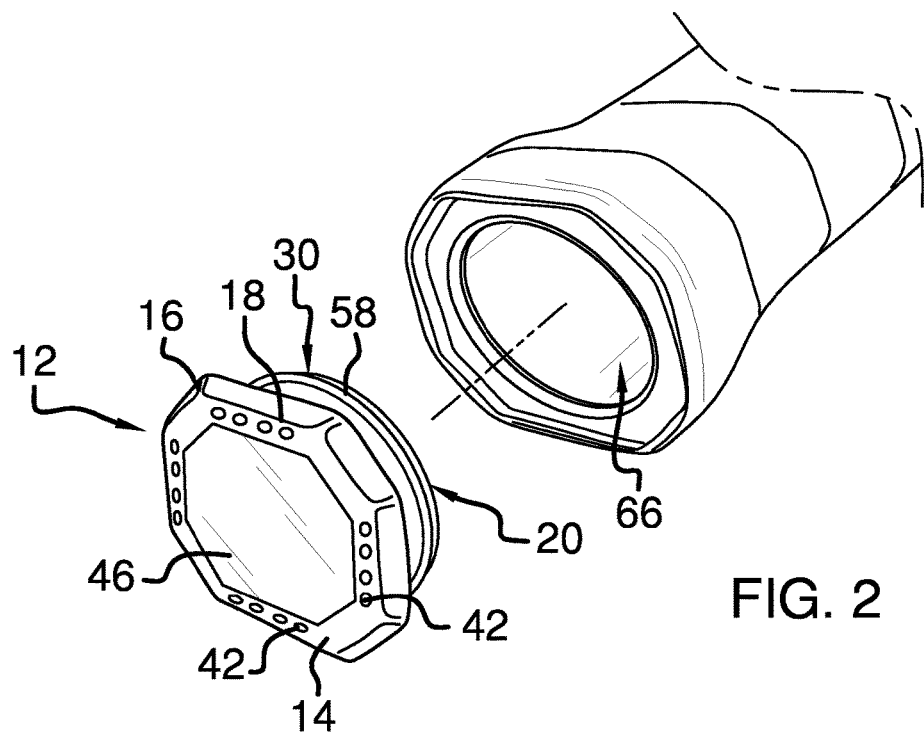
FIG. 2 is a partially exploded top front side perspective view of an embodiment of the disclosure.
Figure 3:
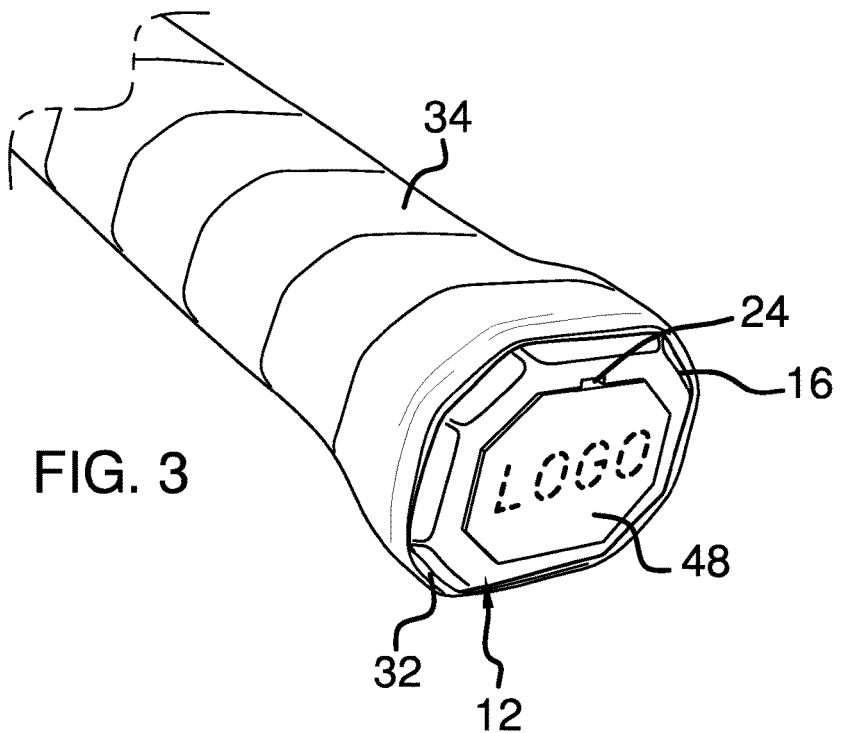
FIG. 3 is a top front side perspective view of an embodiment of the disclosure.
Figure 4:
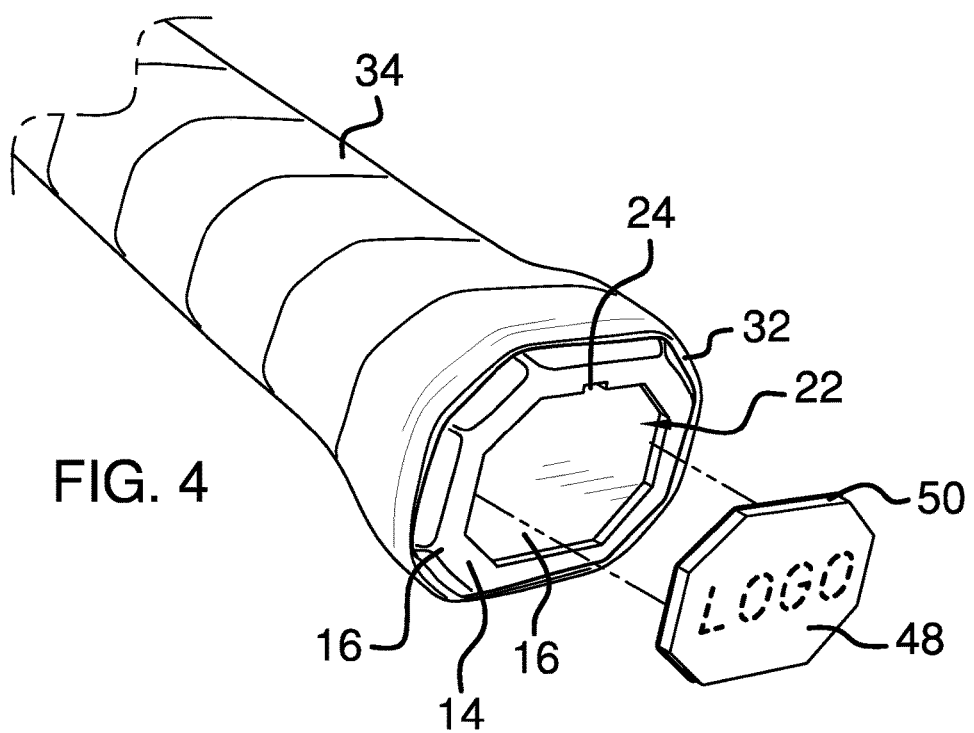
FIG. 4 is a partially exploded top front side perspective view of an embodiment of the disclosure.
Figure 5:
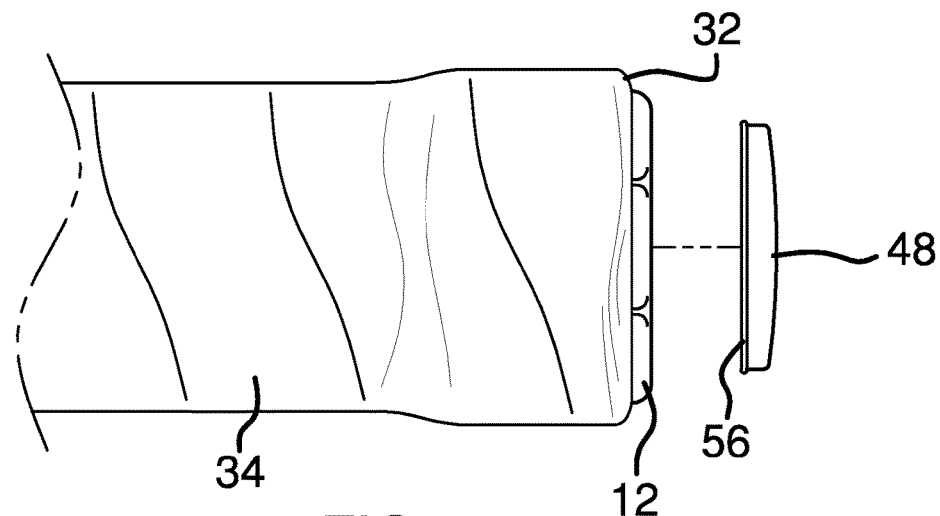
FIG. 5 is a partially exploded side view of an embodiment of the disclosure.

The device 10 may be powered by a conventional battery 68. The battery 68 may be rechargeable through the connection port 80. As shown in FIG. 2, a power switch 82 may be positioned on the first face 14 and electrically coupled to the battery to allow a person to selectively activate and deactivate the device 10.

In use, the housing 12 is coupled to and tracks movement of the racquet 36. The motion data from the motion detector 28 is transmitted or processed to generate data corresponding to calories burned related to the movement or use of the racquet 36.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An activity tracking racquet attachment device comprising:
   a housing having a first face, a perimeter sidewall extending from and around said first face;
   a processor coupled to said housing;
   a motion detector coupled to said housing such that said motion detector detects movement of said housing, said motion detector being communicatively coupled to said processor wherein said processor receives motion data from said motion detector; and
   a coupler coupled to and extending from a second face of said housing wherein said housing is configured for being coupled to an end of a handle of a racquet such that said first face of said housing faces outwardly from the end of the handle of the racquet;
   a display screen coupled to said housing, said display screen being operationally coupled to said processor wherein said processor displays images on said display screen, said display screen being parallel to and inset from said first face of said housing, said housing defining a well extending into said first face of said housing, said display screen being positioned in said well wherein said display screen is visible within said well; and
   a cap, said cap being positionable in said well such that said cap covers said display screen, said cap being removably coupled to said housing for selectively exposing said display screen.

2. The device of claim 1, further comprising a transmitter coupled to said housing, said transmitter being communicatively coupled to said processor wherein said processor transmits said motion data to an extrinsic apparatus.

3. The device of claim 1, further comprising said processor processing said motion data to determine calories burned corresponding to said motion data.

4. The device of claim 1, further comprising a speaker coupled to said housing, said speaker being operationally coupled to said processor wherein said processor broadcasts audio through said speaker.

5. The device of claim 1, further comprising said perimeter sidewall being angled relative to said first face such that said perimeter sidewall extends outward laterally from a peripheral edge of said first face of said housing and towards said second face of said housing.

6. The device of claim 1, further comprising:
   a groove extending into an inwardly facing wall defining said well, said groove being positioned in spaced relationship to said first face of said housing; and
   a lip extending outwardly from a perimeter edge of said cap, said lip being positionable in said groove coupling said cap to said housing.

7. The device of claim 6, further comprising said groove extending a full length around said inwardly facing wall.

8. The device of claim 7, further comprising said lip extending fully around said perimeter edge of said cap.

9. The device of claim 1, further comprising said housing having a notch extending from said well wherein an exposed portion of a perimeter edge of said cap is accessible to facilitate removal of said cap from said well.

10. The device of claim 2, further comprising said transmitter transmitting said motion data using a wireless personal access network.

11. The device of claim 1, further comprising a timer coupled to said housing, said timer being communicatively coupled to said processor.

12. The device of claim 1, further comprising a receiver coupled to said housing, said receiver being communicatively coupled to said processor wherein said processor is controllable from transmissions received by said receiver.

13. An activity tracking racquet attachment device comprising:

a housing having a first face, a perimeter sidewall extending from and around said first face, said perimeter sidewall being angled relative to said first face such that said perimeter sidewall extends outward laterally from a peripheral edge of said first face of said housing and towards said second face of said housing, said housing defining a well extending into said first face of said housing, said housing having a notch extending from said well;

a processor coupled to said housing;

a motion detector coupled to said housing such that said motion detector detects movement of said housing, said motion detector being communicatively coupled to said processor wherein said processor receives motion data from said motion detector, said processor processing said motion data to determine calories burned corresponding to said motion data;

a coupler coupled to and extending from a second face of said housing wherein said housing is configured for being coupled to an end of a handle of a racquet such that said first face of said housing faces outwardly from the end of the handle of the racquet;

a transmitter coupled to said housing, said transmitter being communicatively coupled to said processor wherein said processor transmits said motion data to an extrinsic apparatus, said transmitter transmitting said motion data using a wireless personal access network;

a speaker coupled to said housing, said speaker being operationally coupled to said processor wherein said processor broadcasts audio through said speaker;

a display screen coupled to said housing, said display screen being operationally coupled to said processor wherein said processor displays images on said display screen, said display screen being parallel to and inset from said first face of said housing, said display screen being positioned in said well wherein said display screen is visible within said well;

a cap, said cap being positionable in said well such that said cap covers said display screen, said cap being removably coupled to said housing for selectively exposing said display screen, an exposed portion of a perimeter edge of said cap being accessible through said notch to facilitate removal of said cap from said well;

a groove extending into an inwardly facing wall defining said well, said groove being positioned in spaced relationship to said first face of said housing, said groove extending a full length around said inwardly facing wall;

a lip extending outwardly from a perimeter edge of said cap, said lip being positionable in said groove coupling said cap to said housing, said lip extending fully around said perimeter edge of said cap;

a timer coupled to said housing, said timer being communicatively coupled to said processor; and a receiver coupled to said housing, said receiver being communicatively coupled to said processor wherein said processor is controllable from transmissions received by said receiver.

\* \* \* \* \*